United States Patent
Chan

(10) Patent No.: US 10,231,640 B2
(45) Date of Patent: Mar. 19, 2019

(54) DEVICE FOR DETECTING FULLNESS OF BLADDER

(71) Applicant: Ka Wing Chan, Hong Kong (CN)

(72) Inventor: Ka Wing Chan, Hong Kong (CN)

(*) Notice: Subject to any disclaimer, the term of this patent is extended or adjusted under 35 U.S.C. 154(b) by 334 days.

(21) Appl. No.: 15/054,155

(22) Filed: Feb. 26, 2016

(65) Prior Publication Data

US 2016/0174866 A1   Jun. 23, 2016

Related U.S. Application Data

(63) Continuation-in-part of application No. 13/569,199, filed on Aug. 8, 2012, now abandoned.

(60) Provisional application No. 61/530,391, filed on Sep. 1, 2011.

(51) Int. Cl.
*A61B 5/0488* (2006.01)
*A61B 5/20* (2006.01)
*A61B 5/00* (2006.01)
*A61B 5/107* (2006.01)
A61B 5/024 (2006.01)
A61B 5/0205 (2006.01)

(52) U.S. Cl.
CPC ........ *A61B 5/04882* (2013.01); *A61B 5/1077* (2013.01); *A61B 5/204* (2013.01); *A61B 5/6804* (2013.01); *A61B 5/0205* (2013.01); *A61B 5/02405* (2013.01); *A61B 5/02433* (2013.01); *A61B 5/486* (2013.01); *A61B 5/7282* (2013.01); *A61B 5/746* (2013.01); *A61B 2562/0261* (2013.01); *Y10S 128/905* (2013.01)

(58) Field of Classification Search
CPC .... A61B 2562/0261; A61B 2562/0266; A61B 5/486; A61B 5/7282; A61B 5/746; A61B 5/04882; A61B 5/204; A61B 5/6804; A61B 5/6808; A61B 5/02405; A61B 5/0205; A61F 2013/8476; A61F 2013/8479; A61F 2013/8482; A61F 2013/8485; A61F 2013/8488; A61F 2013/8491; Y10S 128/905
See application file for complete search history.

(56) References Cited

U.S. PATENT DOCUMENTS

| | | | |
|---|---|---|---|
| 6,407,308 B1 * | 6/2002 | Roe | A61B 5/04884 604/361 |
| 8,948,839 B1 * | 2/2015 | Longinotti-Buitoni | A61B 5/6804 29/825 |
| 2007/0252714 A1 * | 11/2007 | Rondoni | A61B 5/0002 340/573.5 |
| 2017/0224280 A1 * | 8/2017 | Bozkurt | A61B 5/6808 |

(Continued)

*Primary Examiner* — David J. McCrosky
(74) *Attorney, Agent, or Firm* — Eagle IP Limited; Jacqueline C. Lui

(57) ABSTRACT

One example embodiment is a device for detecting fullness of a bladder of a subject. The device includes a distension sensor, an electromyography (EMG) sensor and a microcontroller. The distension sensor is located on a waistband of a pant and detects changes to a curvature of skin adjacent the bladder. The EMG sensor is located in the pant and includes two EMG electrodes that detect potential difference caused by contractions of the bladder. The microcontroller processes signals received from the distension sensor and the EMG sensor and generates, based on the signals, an output value that indicates the fullness of the bladder.

17 Claims, 11 Drawing Sheets

(56) References Cited

U.S. PATENT DOCUMENTS

2017/0319849 A1* 11/2017 Su .................... A61N 1/36007

* cited by examiner

DEVICE FOR DETECTING FULLNESS OF BLADDER

BACKGROUND OF INVENTION

Parents want to train their children to go to toilet independently. Such act can increase the self-confidence of the children and it is also the entry requirement for nursery schools. However, most of the current toilet training systems are passive and inefficient. For instance, one of such systems trains children to stay for a certain time on their own potties while they can watch TV and read books on the potties simultaneously. Unfortunately, children usually do not want to go to toilet because they do not have enough urine or they have already discharged urine before the training and so toilet training fails. Also, children usually fails to show clear signal of urination to the parents until the very last moment and so parents cannot run the training as expected effectively; thus they may need an indicator for indicating the fullness of the children's bladders.

Devices for measuring the volume of urine in bladders are available. For example, U.S. Pat. No. 5,058,591 and U.S. Pat. No. 4,926,871 disclose techniques for the measurement of the volume of a human bladder utilizing ultrasound transducer. However, the implementation of ultrasonic transducer in such device may make it expensive and too bulky to be readily installed on children or ones in need thereof, and may also interrupt their movement.

SUMMARY OF INVENTION

In light of the foregoing background, it is an object of the present invention to provide a device to facilitate the monitoring of distention level of the bladder.

One example embodiment is a device for detecting fullness of a bladder of a subject. The device includes a distension sensor, an electromyography (EMG) sensor and a microcontroller. The distension sensor is located on a waistband of a pant and detects changes to a curvature of skin adjacent the bladder. The EMG sensor is located in the pant and includes two EMG electrodes that detect potential difference caused by contractions of the bladder. The microcontroller processes signals received from the distension sensor and the EMG sensor and generates, based on the signals, an output value that indicates the fullness of the bladder.

There are many advantages to the present invention. For instance, in a toilet training program, upon attaching the device described in the present invention to the children, parents will easily be alerted by the device when the bladders of their children are full, so that they can take them to the toilet or assist them in toilet training. As such, children will learn how to do independent toileting quickly with more confidence.

Besides, the small size of the device allows the user to move more freely without much hindrance. It is also inexpensive and easy to operate.

There are some other advantages of the present invention. For example, some children suffer from bedwetting, and example embodiments can assist parents in determining when the bladder of the children is full even while the children sleep. At night for example, parents can wake a child and take him or her to the toilet when the system notifies the parent that the bladder of the child is full or near full and thus avoid bedwetting.

Apart from children, the device of the present invention is also suitable for other people, such as patients suffering from uncontrollable urination, incontinence, physically disabled patients, and/or comatose patients. For example, users of the present invention can reduce or eliminate a need to wear an adult diaper or adult nappy since the device provides a warning or alert when the bladder is full or becoming full.

Pet owners can also find the device useful in toilet training their pets on how to use their pet potties to avoid soiling a house or public area.

DETAILED DESCRIPTION OF THE INVENTION

As used herein and in the claims, "comprising" means including the following elements but not excluding others.

Figure 1:
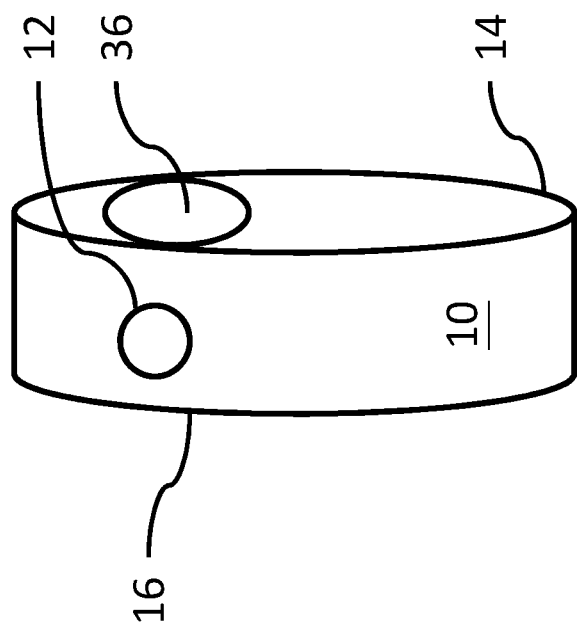
FIG. 1 is a schematic illustration of a device according to one embodiment of the present invention.

Referring first to FIG. 1, the first embodiment of the present invention is a device 10 for detecting the curvature change of the skin surface of a human or an animal subject comprising a housing 14 in which a sensing unit 30 and a processing unit 31 (not shown in FIG. 1) are disposed therein.

In an exemplary embodiment of the present invention, the housing 14 comprises a film 16. The outside surface of the film 16 is attached to a pre-determined area of the subject when the device 10 is in use, while on the inside surface of the film 16, the sensing unit 30 is disposed thereon. In one exemplary embodiment, the pre-determined area is the area of the lower abdominal region of a human above the pubic bone and in close proximity to the bladder. The film 16 is made of material soft enough to allow the sensing unit 30 to effectively detect the curvature change of the pre-determined area.

In a further exemplary embodiment, the housing 14 is made of water-proof material and/or biocompatible material to protect the device 10 from potential contamination by urine as such contamination may cause current leakage of the device.

In another exemplary embodiment of the present invention, the device 10 further comprises a fastening unit for flexibly attaching the device to the pre-determined area. In a further exemplary embodiment, the fastening unit is made of an adhesive and biocompatible material and disposed on the outside of the film 16.

In an exemplary embodiment of the present invention as illustrated in FIG. 1, an indicating subunit 36 is disposed on the housing 14 for generating a visual signal (in which case the indicating subunit 36 may be a display or an LED light), an audio signal (in which case the indicating subunit 36 may be a speaker), or any combination thereof.

Figure 2:
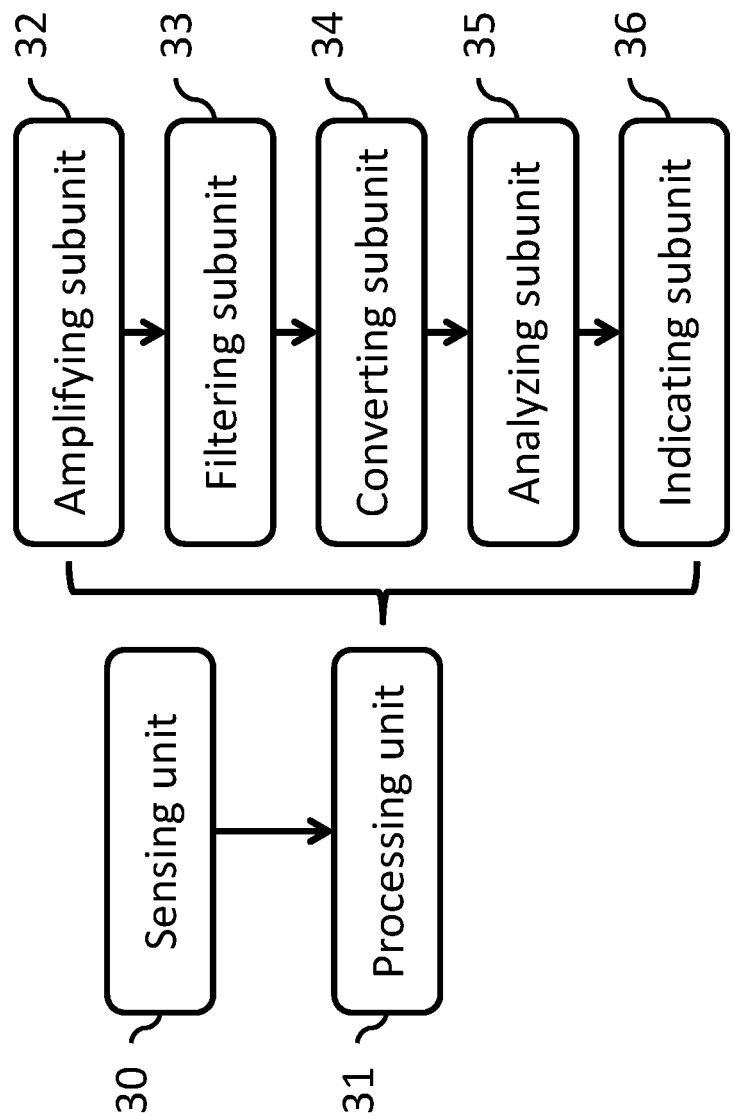
FIG. 2 is a block diagram showing the major components and the connection thereof for a device according to the same embodiment of the present invention.

Referring now to FIG. 2, the sensing unit 30 is a sensor for detecting the curvature change of the pre-determined area and generating data for the curvature change. In another exemplary embodiment, the generated data for the curvature change is an analog signal.

The processing unit 31 is connected to the sensing unit 30 for receiving the data generated from the sensing unit 30. It triggers the generation of an indication signal when the data is beyond a pre-defined threshold value.

In a further exemplary embodiment, the processing unit 31 further comprises an amplifying subunit 32, a filtering subunit 33, a converting subunit 34, an analyzing subunit 35 and an indicating subunit 36. In one exemplary embodiment as illustrated in FIG. 2, the filtering subunit 33 is connected to the amplifying subunit 32; the converting subunit 34 is connected to the filtering subunit 33; the analyzing subunit 35 is connected to the converting subunit 34; and the indicating subunit 36 is connected to the analyzing subunit 35.

Figure 3:
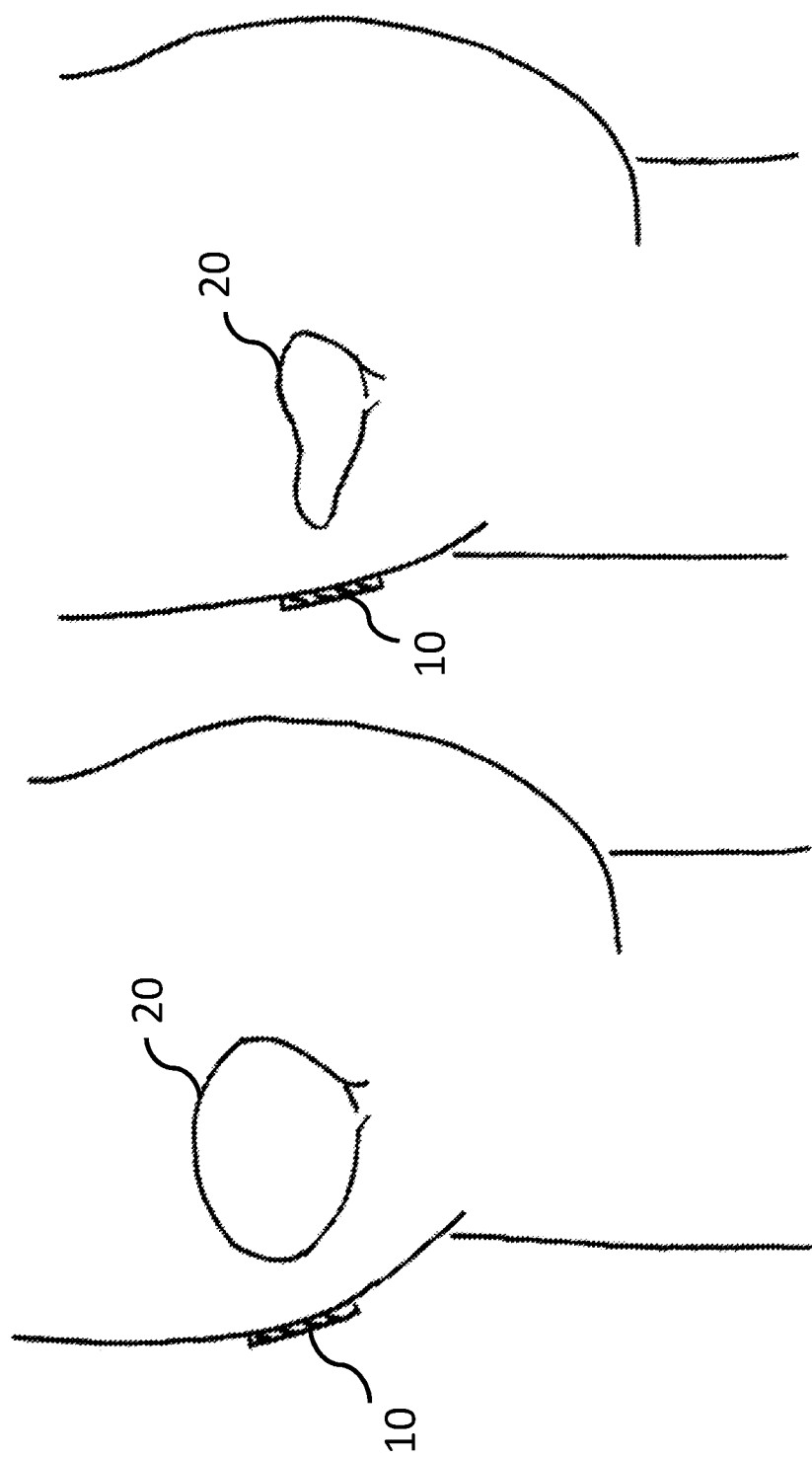
FIGS. 3a and 3b illustrate the device in use when it is attached to the pre-defined location of the subject in need thereof according to the same embodiment of the present invention.

During operation, the device 10 is attached to the pre-determined area for detecting the curvature change of that area. In the exemplary embodiment as shown in FIGS. 3a & 3b, the device 10 is placed in the lower abdominal region of the human subject. The bladder is in the state of fullness or near fullness in FIG. 3a and in the state of emptiness or near emptiness in FIG. 3b.

Figure 4:
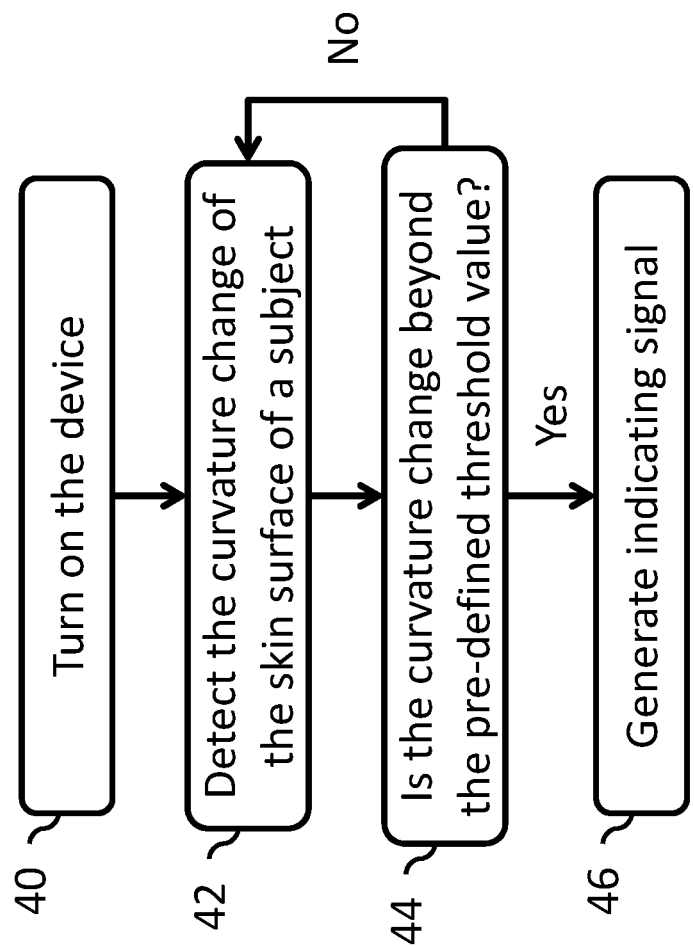
FIGS. 4a and b illustrate flow diagrams of the main operation steps of the device according to two embodiments of the present invention.
Figure 4:
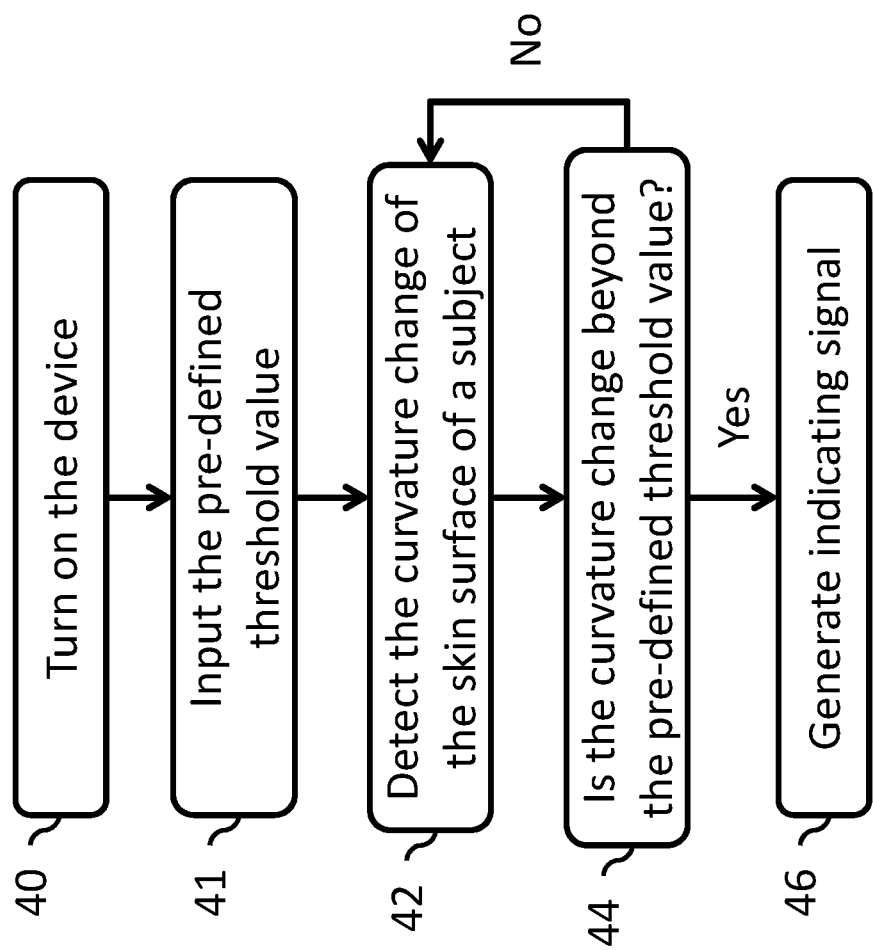

In an exemplary embodiment, the flow of operation of the device 10 is shown in FIGS. 4a & 4b. Upon switching on the device 10 (box 40), the sensing unit 30 begins to detect the curvature change of the pre-determined area (box 42) and a data representative of the curvature change is generated by the sensing unit 30. The data is then transmitted to the processing unit 31 and checked whether it is beyond the pre-defined threshold value (box 44). In the scenario that the data exceeds the pre-defined threshold value, the processing unit 30 is triggered to generate the indication signal (box 46).

In a further exemplary embodiment, upon being transmitted to the processing unit 31, the data is amplified by the amplifying subunit 32 and filtered by the filtering subunit 33. The filtered data is converted by the converting subunit 34 into a form analyzable by the analyzing subunit 35 and is compared with the pre-defined threshold value. A working signal is generated by the analyzing subunit 35 and transmitted to the indicating subunit 36 when the converted data is beyond the pre-defined threshold value. The indicating subunit 36 then generates the indication signal on receiving the working signal from the analyzing subunit 35. The aforesaid data flow inside the processing unit 31 is shown in FIG. 2 for ease of illustration.

In an exemplary embodiment of the present invention as illustrated in FIG. 1, a switch 12 is disposed on the housing 14 for switching on/off and/or resetting the device 10.

In an exemplary embodiment, the pre-defined threshold value can be pre-set in the device 10 or can be inputted by the user (box 41) as shown in FIG. 4b. In another exemplary embodiment, the pre-defined threshold value is determined based on the clinical data from a large number and variety of subjects, such as children, physical disabled patients and pets. In another exemplary embodiment, the pre-defined threshold value is tailor-determined for a particular subject based on the physiological data of that subject.

In yet another exemplary embodiment, in defining the threshold value, the state of an empty bladder is first recorded, followed by calculating the threshold value based on a mapping table. In one exemplary embodiment, the mapping table for different types of subjects is shown in Table 1. The threshold may be set as 6 for a child, 4.7 for an adult, or 11.4 for a pet. In another exemplary embodiment, the pet used in the construction of the mapping table (Table 1) is a dog.

TABLE 1

A mapping table for calculating the threshold value

| Degree of Curvature | Sensor Output (Voltage) | Threshold (Voltage) | | |
|---|---|---|---|---|
| | | Child | Adult | Pet |
| (Flat) 1 | 0.01 | 5.0 | 4.0 | 10.0 |
| 2 | 0.02 | 5.0 | 4.0 | 10.2 |
| 3 | 0.03 | 5.0 | 4.2 | 10.4 |
| 4 | 0.04 | 5.5 | 4.2 | 10.6 |
| 5 | 0.05 | 5.5 | 4.5 | 10.8 |
| 6 | 0.06 | 5.5 | 4.5 | 11.0 |
| 7 | 0.07 | 5.5 | 4.7 | 11.2 |
| 8 | 0.08 | 6.0 | 4.7 | 11.4 |
| 9 | 0.09 | 6.0 | 4.9 | 11.6 |
| (Bended) 10 | 0.1 | 6.0 | 4.9 | 11.8 |

In another exemplary embodiment of the present invention, the indication signal is transmitted via a wireless transmission (e.g. radio frequency transmission) to an external device such as a computer, a mobile device with a wireless receptor or any combination thereof. In view of the aforesaid description, the application of the device of the instant invention can be extended to the aspect of toilet training for children and pets. For instance, the device 10 can be attached to the lower abdominal region, in close proximity of the bladder, of a child or a pet for detecting the curvature change of that region. When the curvature change is beyond a pre-defined threshold value, referring to the state in which the bladder is full or nearly full, an indication signal is generated to alert the parents or pet owners to take corresponding training actions, for example, taking the child to toilet or the pet to the pet potty.

The preferred embodiments of the present invention are thus fully described. Although the description referred to particular embodiments, it will be clear to one skilled in the art that the present invention may be practiced with variation of these specific details. Hence this invention should not be construed as limited to the embodiments set forth herein.

For example, the external device to receive the transmitted indication signal may be designed to be located in the vicinity of the subject or person taking care of the subject, which may be a wrist-mounted device with a wireless receptor worn by the subject or the caretaker. The wrist-mounted device can generate an alert to the subject or the caretaker when the device detects that the curvature change is beyond the threshold value.

Also, it may be clear to one skilled in the art that a specific operation method to switch on/off the device to avoid it being mistakenly switched on/off can be designed. For instance, a double-press or a long-press on the switch can be designed as the operating signal to the device.

Example embodiments relate to a device and method that detects fullness of a bladder of a subject, which includes one or more sensors and a microcontroller. The sensors and the microcontroller are located in a pant.

An example embodiment includes a distension sensor that detects a curvature change of skin adjacent the bladder of the subject, and an electromyography (EMG) sensor that detects potential difference caused by contractions of the bladder of the subject. The distension sensor includes a strain gauge for measuring distension of a lower abdomen of the subject. The EMG sensor includes two electrodes for detecting an EMG signal and sending the EMG signal to the microcontroller.

In one embodiment for example, the microcontroller processes signals from the distension sensor and the EMG sensor, and generates an output value that indicates fullness of the bladder. The output value is calculated based on statistical parameters of the subject (such as one or more of age, height, gender, weight, etc.) and dynamic parameters of the subject (such as one or more of curvature of the skin adjacent the bladder, EMG signal, etc.).

In an example embodiment, the device includes a heart sensor that detects a heart rate variability (HRV) of a heart of the subject. The microcontroller processes signals from the heart sensor with the signals from the other two sensors to generate the output value.

An example embodiment includes an alert module that communicates with the microcontroller. When the fullness of the bladder reaches a threshold value, the alert module produces an audio alert, a visual alert, or takes another action (such as wirelessly transmitting an alert to another electronic device).

Figure 5:
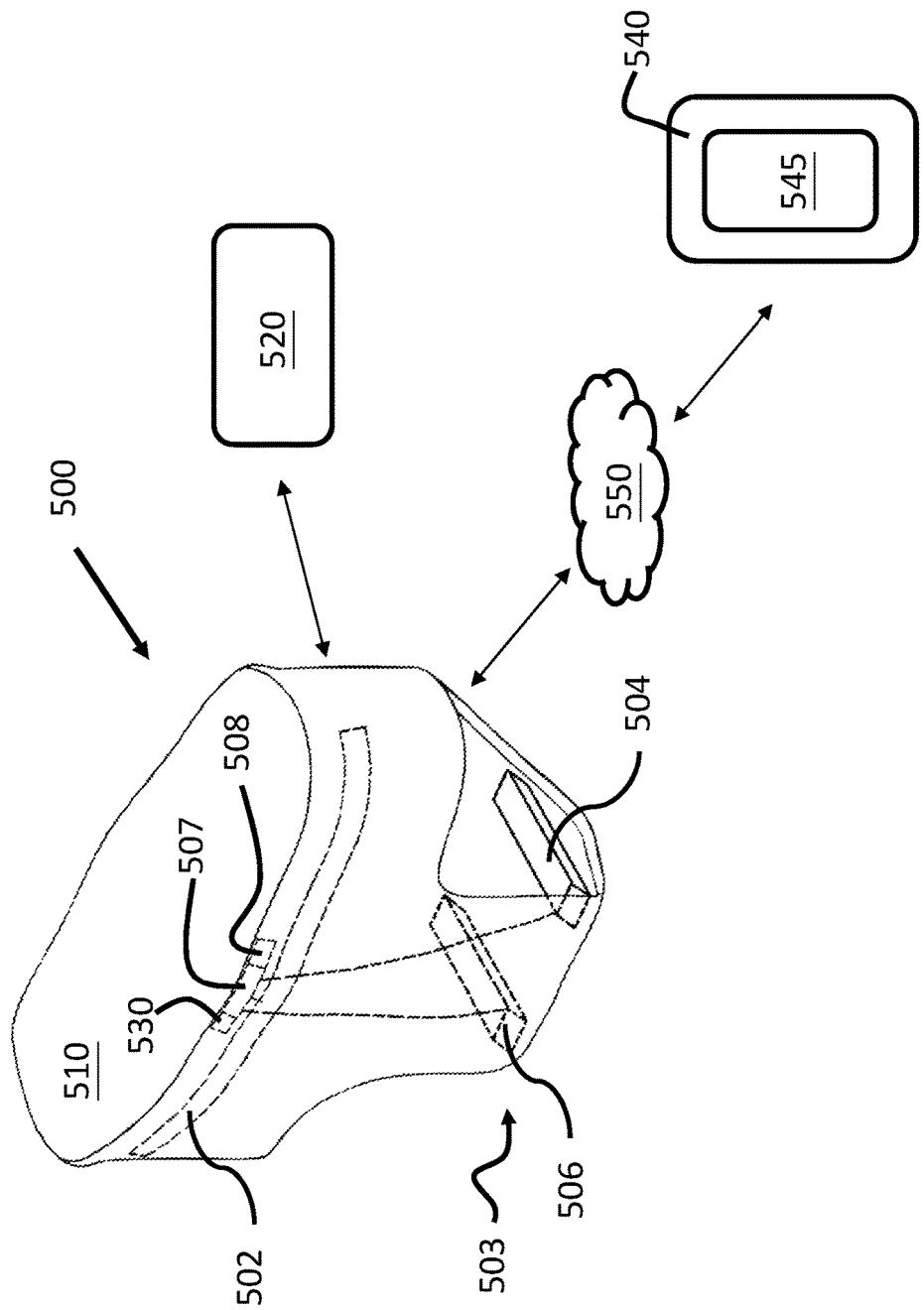
FIG. 5 shows a device that detects fullness of a bladder of a subject in accordance with an example embodiment.

FIG. 5 shows a device 500 that detects fullness of a bladder of a subject. A distension sensor 502 is located on or in a waistband of a pant 510 and has an elongated rectangular shape. The distension sensor detects changes to a curvature or distension of skin adjacent the bladder in a lower abdominal area of the subject, such that fullness of the bladder can be determined noninvasively.

An EMG sensor 503 includes two EMG electrodes 504 and 506 in which the EMG electrodes are located on two opposite sides of a crotch of the pant. The EMG electrodes are made of conductive material, for example, commercially available Ag/AgCl electrode, silver plate, fabric with carbon. The EMG sensor 503 detects potential difference caused by contractions of the bladder of the subject, such that fullness of the bladder can be determined noninvasively.

An electronic device 507 includes a microcontroller 508 located on the upper edge of the pant in which it physically and electrically connects with the distension sensor 502 and the two EMG electrodes 504/506 via a wire or flex cable. The microcontroller generates, based on the signals received from the distension sensor and the EMG sensor, an output value that indicates the fullness of the bladder.

In an example embodiment, the output value indicates a percentage or an amount of the fullness of the bladder.

In another example embodiment, a heart sensor 520 detects a heart rate variability (HRV) of a heart of the subject and transmits sensed information to the microcontroller 508. The microcontroller processes signals received from the heart sensor to generate the output value that indicates the fullness of the bladder such that fullness of the bladder can be determined noninvasively.

The heart sensor 520 can directly connect to the microcontroller via a wire or flex cable. Alternatively, the heart sensor includes a transmitter that wirelessly transmits its sensed data to the microcontroller. Furthermore, the heart sensor can be located in the pant 510 or located adjacent the pant, such as being worn by the subject or provided in a garment worn by the subject.

In an example embodiment, the microcontroller generates the output value based on static parameters of the subject and dynamic parameters of the subject. By way of example, static parameters include, but are not limited to, age, weight, height, waist, gender, etc. Dynamic parameters include, but are not limited to, signals received from the distension sensor, the EMG sensor, the heart sensor, or another sensor or electronic device.

In another example embodiment, the device includes an alert module 530 that communicates with the microcontroller 508 and generates an alert, such as an audio, visual or vibrational alert when the fullness of the bladder reaches a threshold value. The threshold value can be predetermined, adjusted, or set by a person or an electronic device.

FIG. 5 shows the alert module 530 being located adjacent to or included with the electronic device 507 and/or microcontroller 508. The alert module, however, can be located in other location as well, such as being located in the pant away from the microcontroller, located with or adjacent a sensor, or located elsewhere in the pant or outside of the pant.

The microcontroller 508 can wirelessly transmit data to another electronic device 540 via a network 550 or transmit this data directly to the electronic device, such as transmitting the information via BLUETOOTH or another short range wireless standard. The electronic device 540 (such as a computer, a server, smartphone, laptop, or handheld portable electronic device) can include a display 545 that displays information, such as received data from the microcontroller, alerts, fullness indications of the bladder, etc.

Figure 6:
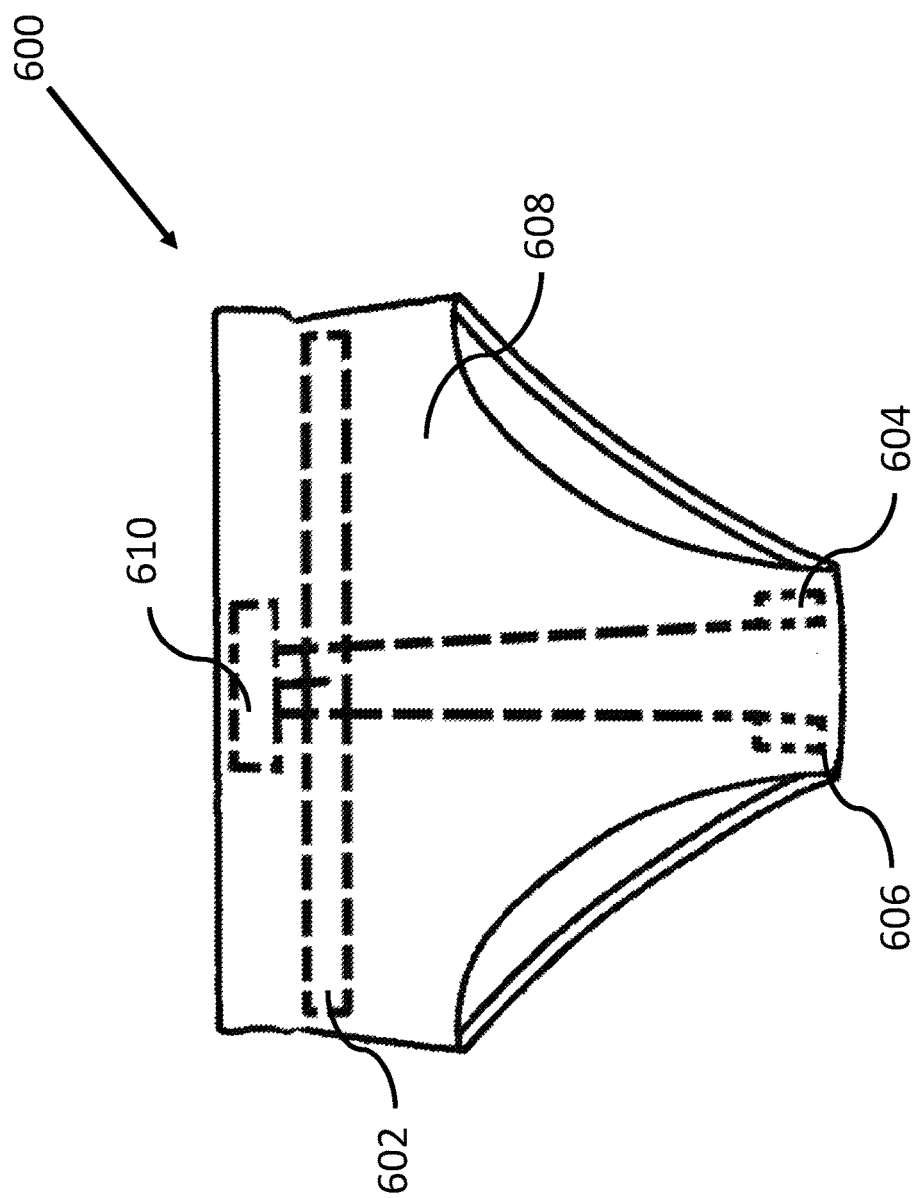
FIG. 6 shows an undergarment or a pant that detects fullness of a bladder of a person in accordance with an example embodiment.

FIG. 6 shows an undergarment or a pant 600 that detects fullness of a bladder of a person. A distension sensor 602 is located at the waistband of the undergarment and senses a curvature of the bladder. An EMG sensor includes two EMG electrodes 604/606 located on each side of the crotch of the undergarment. The EMG sensor senses changes in electric potential of the bladder. A microcontroller 608 is located near the upper opening of the undergarment and analyzes data received from the EMG sensor and the distension sensor, and determines the fullness of the bladder.

In an example embodiment, the microcontroller generates an output value that indicates the fullness of the bladder based on static parameters of the person and data from the distention sensor and the EMG sensor. By way of example, static parameters include age, weight, height, waist, gender, etc.; dynamic parameters include signals received from the distension sensor or the EMG sensor.

In another example embodiment, the undergarment includes an infrared sensor that measures a heart rate variability (HRV) of the person. The microcontroller communicates with the infrared sensor and analyzes data on the HRV of the person to determine the fullness of the bladder.

In one example embodiment, the undergarment includes an alert module that vibrates when the microcontroller determines that the fullness of the bladder of the person reaches a threshold value. The threshold value is predetermined by a user of the undergarment.

In an example embodiment, the undergarment includes a wireless transmitter that transmits an alert signal to an electronic device in wireless communication with the wireless transmitter when the microcontroller determines that the fullness of the bladder of the person reaches a threshold value.

Figure 7:
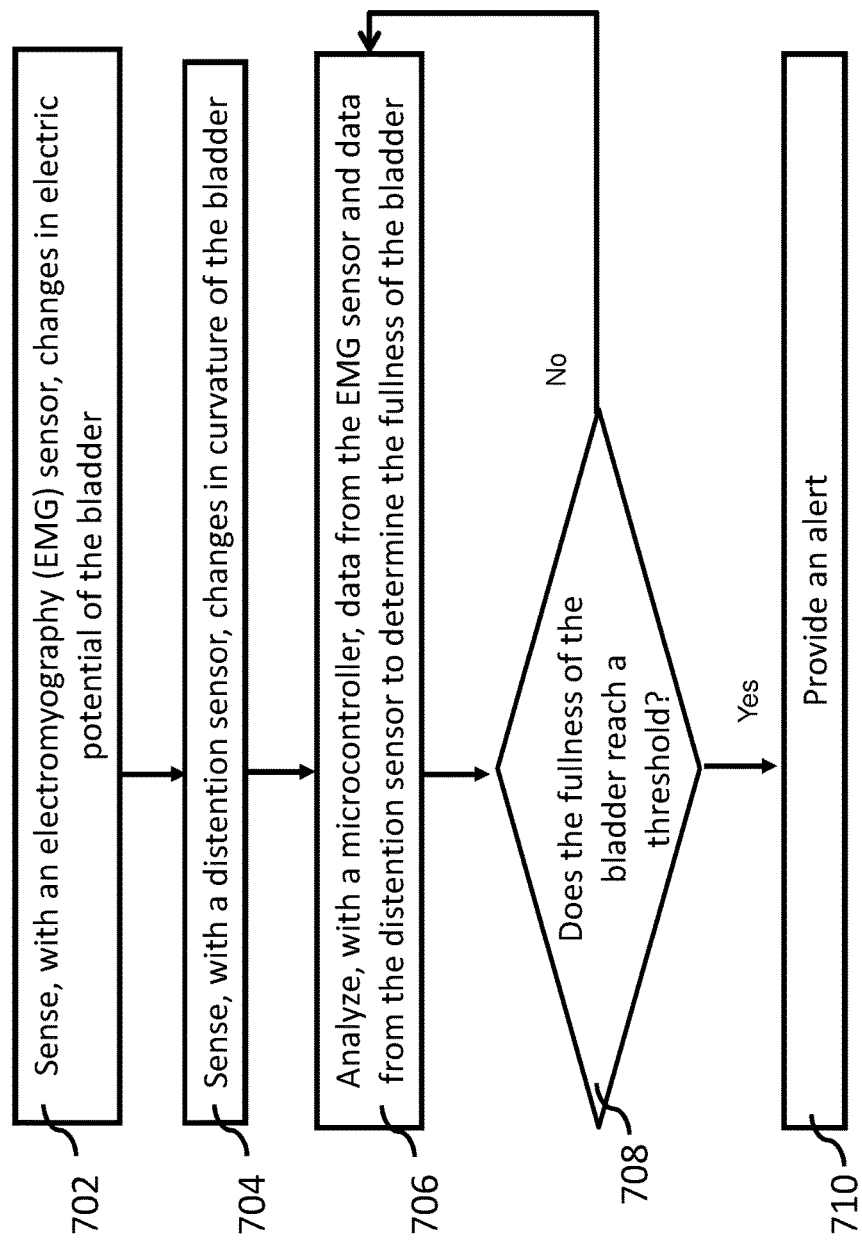
FIG. 7 shows a method of measuring a fullness of a bladder of a person wearing an undergarment in accordance with an example embodiment.

FIG. 7 shows a method of measuring a fullness of a bladder of a person wearing an undergarment. Changes in electric potential of the bladder are sensed with an electromyography (EMG) sensor provided in the undergarment 702. Changes in curvature of the bladder of the person are sensed with a distension sensor provided in the undergarment 704. Data from the EMG sensor and data from the distension sensor are analyzed, with a microcontroller provided in the undergarment, to determine the fullness of the bladder 706. When the fullness of the bladder of the person reaches a threshold value 708, an alert module provided in the undergarment will generate an alert 710. On the other hand, when the fullness of the bladder of the person does not reach a threshold value 708, the microcontroller will continue analyzing the data from the EMG sensor and the distension sensor 706.

Figure 8:
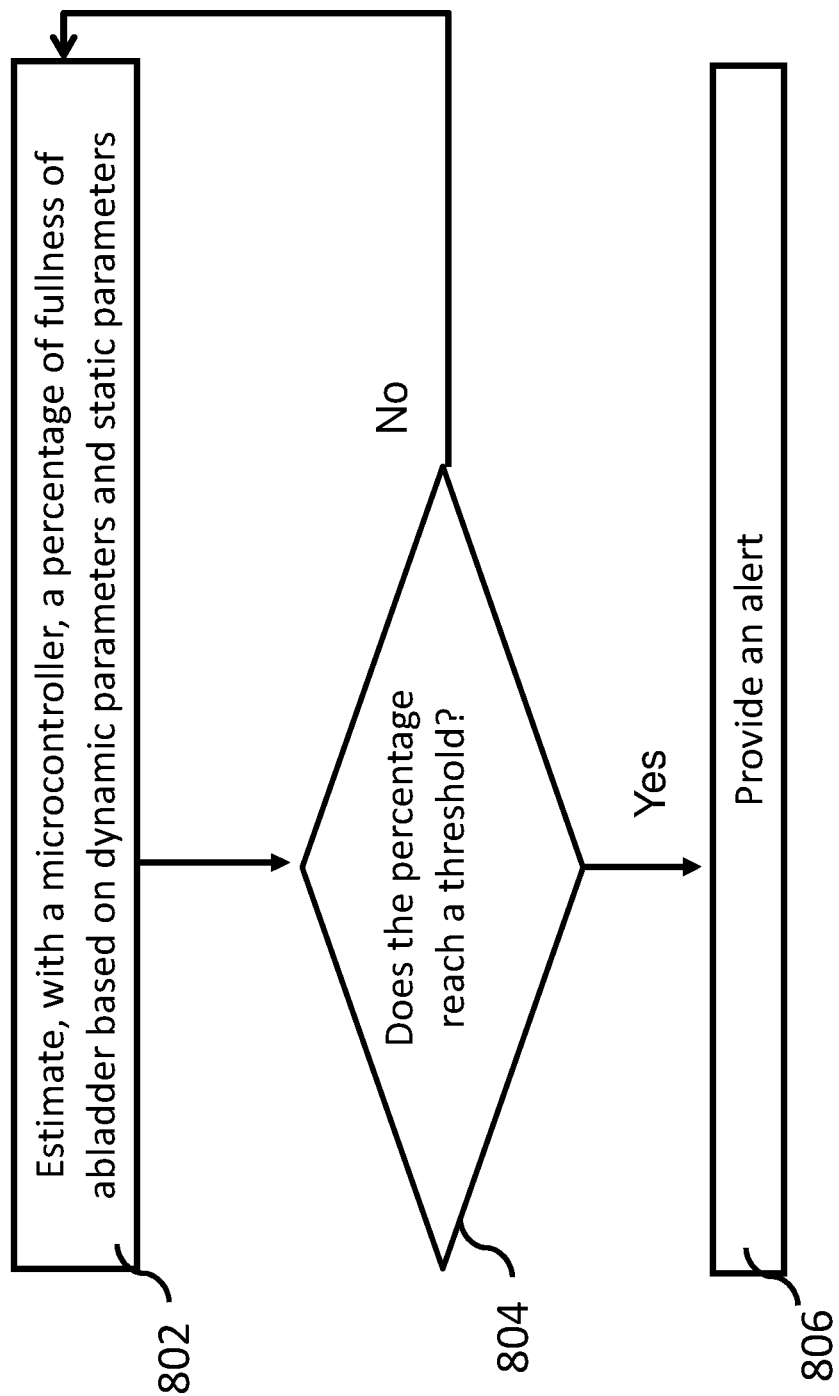
FIG. 8 shows an embodiment of a method of estimating a percentage of the fullness of the bladder of the person based on dynamic parameters and static parameters in accordance with an example embodiment.

FIG. 8 shows an embodiment of the method, in which the microcontroller estimates a percentage of the fullness of the bladder of the person based on dynamic parameters and static parameters 802. Dynamic parameters include the data from the EMG sensor and the data from the distension sensor, while static parameters include data of an age of the person, a gender of the person, a weight of the person, a height of the person and a waist of the person. When the percentage reaches a threshold value 804, an alert module provided in the undergarment will generate an alert 806. On the other hand, when the percentage does not reach a threshold value 804, the microcontroller will continue estimating the percentage based on dynamic parameters and static parameters 802.

Figure 9:
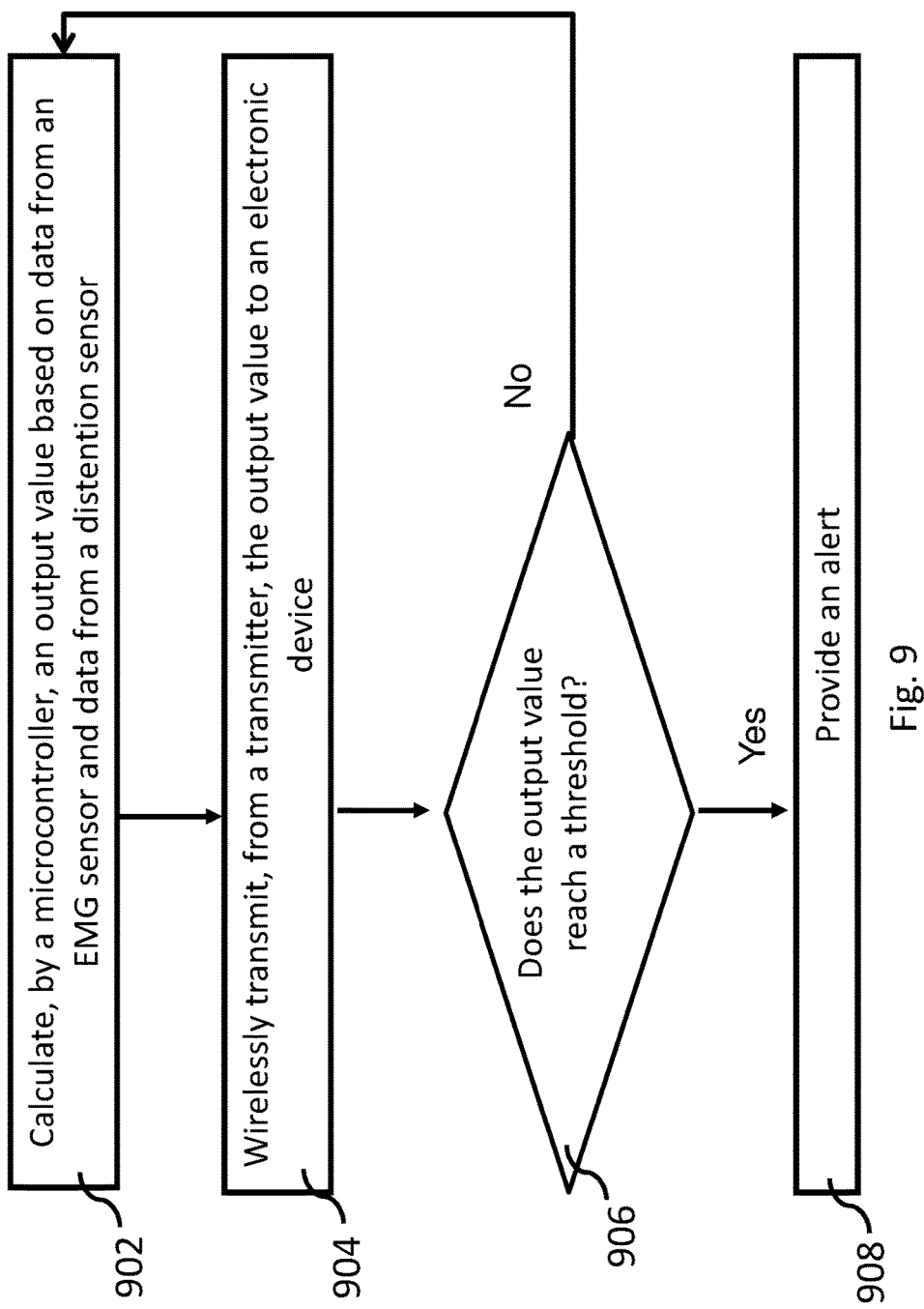
FIG. 9 shows another embodiment of a method of calculating an output value based on the data from the EMG sensor and the data from the distension sensor in accordance with an example embodiment.

FIG. 9 shows another embodiment of the method, in which the microprocessor calculates an output value based on the data from the EMG sensor and the data from the distension sensor 902. A transmitter provided in the undergarment wirelessly transmits the output value to an electronic device that is external from the undergarment 904. The output value provides an indication of the fullness of the bladder. When the output value reaches a threshold value 906, an alert module provided in the undergarment will generate an alert 908. On the other hand, when the output value does not reach a threshold value 906, the microcontroller will continue calculating the output value based on the data from the EMG sensor and the data from the distension sensor 902.

Figure 10:
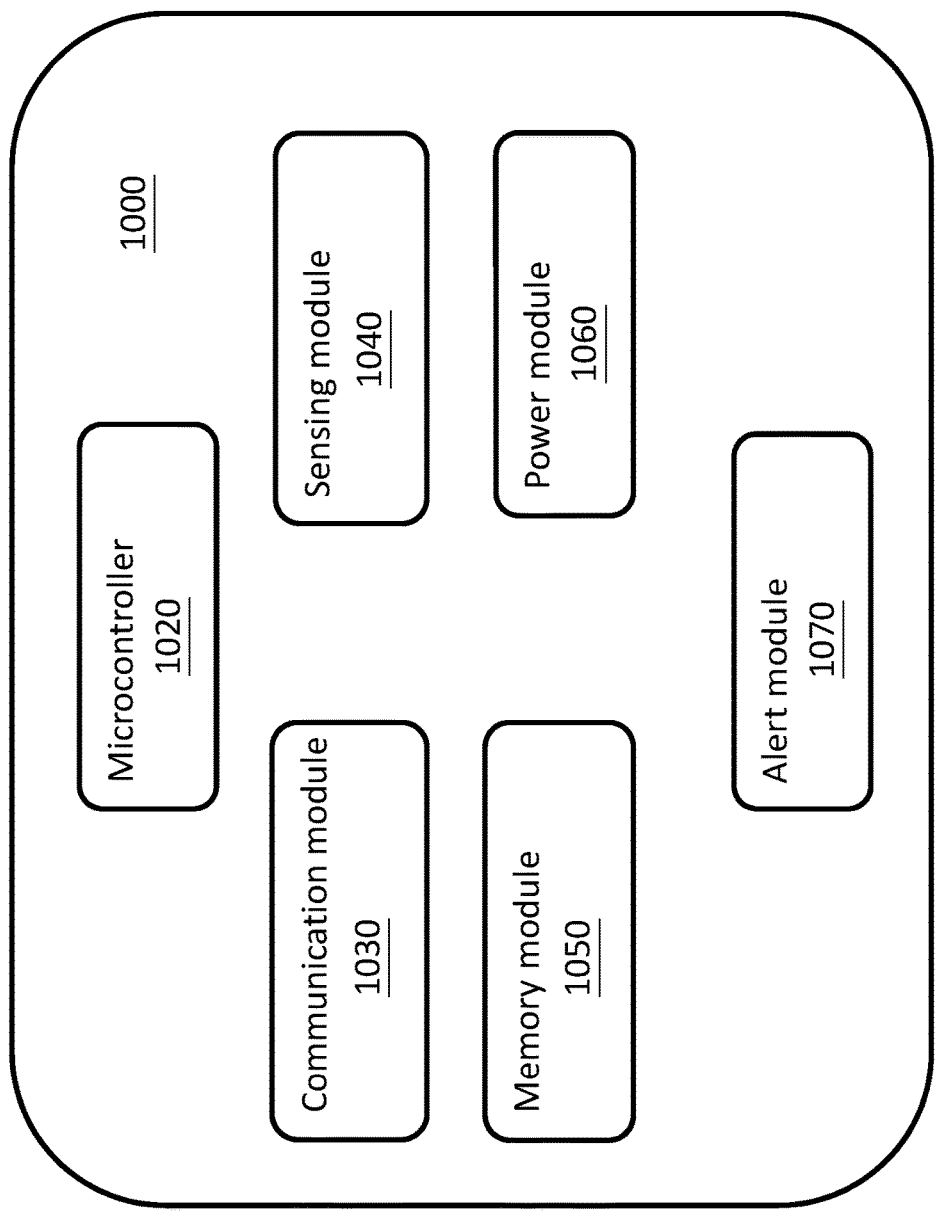
FIG. 10 shows an embodiment of an electronic device in accordance with an example embodiment.

FIG. 10 shows an electronic device 1000 in accordance with an example embodiment. The electronic device 1000 can be included in the pant of the subject, such as being provided at 507 shown in FIG. 1.

The electronic device 1000 includes a microcontroller 1020 that communicates with a communication module 1030, a sensing module 1040 (including one or more sensors discussed herein), a memory module 1050, a power module 1060, and the alert module 1070. The communication module 1030 transmits information from the microcontroller 1020 to an external and/or remote electronic device. The sensing module 1040 detects the signals from any of the aforementioned sensors. In one example embodiment, an accelerometer embedded within or in communication with the communication module 1030 receives signal due to unexpected signal from motion artefact. The memory module 1050 records a weighting parameter and data history. The power module 1060 includes a charging circuit that provides power to the device via wireless charging or micro USB.

In another example embodiment, the electronic device includes a transmitter that communicates with the microcontroller and that wirelessly transmits the output value to an electronic device. The electronic device, being remote from the device, indicates the fullness of the bladder.

In an example embodiment of the method, a heart rate variability (HRV) of the person is sensed with an infrared sensor provided in the undergarment. Data from the infrared sensor is analyzed, with a microcontroller provided in the undergarment, to determine the fullness of the bladder.

In another example embodiment of the method, a vibrational alert is generated by a vibration sensor provided in the undergarment when the fullness of the bladder of the person reaches a threshold value.

In one example embodiment of the method, the EMG sensor is positioned in the undergarment such that the EMG sensor is located adjacent an anus of the person when the undergarment is worn by the person.

It will be appreciated that a number of methods or algorithms can be used to determine the fullness of the bladder of the person. By way of example, one method to calculate the fullness of the bladder is based on static parameters and dynamic parameters of the person. A formula for calculating an output value that indicates the fullness of the bladder is shown in the Equation I below:

$$\text{Output Value}=\Sigma(W_n \times P_n) \quad \text{(Equation I)}$$

Where, $P_n$ denotes a static parameter or a dynamic parameter and $W_n$ denotes a weighting parameter for a corresponding static parameter or dynamic parameter. Dynamic parameters include data from the EMG sensor, data from the distension sensor, and data from the infrared sensor. Static parameters include data of an age of the person, a gender of the person, a weight of the person, a height of the person and a waist of the person.

A study was carried out in using the algorithm for determining the fullness of a bladder of a person, with procedural detail and results discussed as follows.

In this study, the following Equation II is used to calculate the output value that indicates a percentage of the fullness of the bladder:

$$\text{Output Value}=W1\times\text{Age}+W2\times\text{Weight}+W3\times\text{Height}+\\ W4\times\text{Waist}+W5\times\text{Gender}+W6\times\text{Distension}+W7\times\\ \text{Amplitude of EMG}+W8\times\text{Heart Rate Variability} \quad \text{(Equation II)}$$

This study was carried out with one subject (A) and a static part of Equation II (i.e. sum of W1×Age+W2×Weight+W3×Height+W4×Waist+W5×Gender) remains constant throughout the study.

The weighting parameters of the dynamic parameters of Equation II (i.e. W6, W7 and W8) are first calibrated before the start of the study. The calibration includes four stages, namely two stages of high desire of urination and two stages of low desire of urination. Data from the calibration is summarized in Table 2 below.

TABLE 2

Calibration Data for Dynamic Part of Equation II

| | Static Part | | | | | Dynamic Part | | | |
| | | | | | | Distention | HRV | Amplitude | |
| Stage | Age (y) | Height (cm) | Weight (kg) | Waist (cm) | Gender | Voltage (1.5-2.3 V) | RMMSD (ms) | of EMG (2-10 mV) | Total Mark |
|---|---|---|---|---|---|---|---|---|---|
| High Desire of Urination | 38 | 183 | 88 | 97 | 1 | 3.41 | 18 | 9.5 | 83 |
| After Urination | 38 | 183 | 88 | 97 | 1 | 1.5 | 6 | 3 | 23 |
| High Desire of Urination | 38 | 183 | 88 | 97 | 1 | 3.3 | 17 | 8.8 | 80 |
| After Urination | 38 | 183 | 88 | 97 | 1 | 1.5 | 8 | 3.5 | 25 |

After calibration, the static part of Equation II and the weighting parameters of the dynamic parameters of Equation II are estimated, resulting in Equation III below:

Output value=−22+31*Distension+1.77*Heart Rate Variability−3.07*Amplitude of ECG          (Equation III)

By applying Equation III, the output values indicating different fullness of the bladder of the subject A (in percentage of fullness of the bladder) are calculated and the results are summarized in Table 3 below.

TABLE 3

Calculation of Output Value by Equation III

| Case | Status | Distention Voltage (1.5-2.3 V) | HRV RMMSD (ms) | Amplitude of EMG (2-10 mV) | Output Value (%) |
|---|---|---|---|---|---|
| 1 | High Desire of Urination | 3.3 | 16 | 8.5 | 79 |
| 2 | After Urination | 2 | 10 | 4.4 | 41 |
| 3 | Less Desire of Urination | 2.9 | 14 | 8.2 | 72 |
| 4 | After Urination | 1.8 | 8 | 4 | 33 |

The threshold value is predetermined by the user. For example, if the threshold value is set at 75%, an alert signal is generated in Case 1 only. However, if the threshold value is set at 70%, an alert signal is generated in Case 1 and Case 2.

In practice, the threshold value is determined based on clinical data with a large number of children. The threshold value for adults will be changed.

When the threshold value is achieved, the device will provide alert signal to an external device. An alert signal can be a light (such as a LED light), a sound or a vibrational signal to alert a user to go to the toilet. Users can set the threshold value to a lower value so as to offer some buffer time to ensure that the users have sufficient time to go to toilet. In that case, the self-esteem for the elderly users can be retained and toilet training time for babies can be shortened.

The device is charging and the whole device will stop running. When the charging is completed, the device will be in sleep mode. When the heart rate is detected, it will start to record all the physiological data. The purpose of this function is to save the power.

As used herein, a "curvature of a bladder" is a curvature of skin adjacent the bladder and it is directly varied with fullness of the bladder. An elastic bladder is important for storing increasing volumes of bladder urine at low pressure. This means that the bladder is expanding when the volume of urine in the bladder is increasing. The expansion of the bladder can increase the size of the bladder, for example but not limited to, from about 2 inches to more than 5 inches depending on the amount of liquid. A typical human bladder reaches its capacity between 16 to 24 ounces of urine. That means when the bladder is full and it will increase the curvature of the bladder.

As used herein, a "heart rate variability (HRV)" is variation in the time interval between heartbeats. HRV may affect the imbalance of the autonomic nervous system. With an empty bladder, a person has lower parasympathetic nerve activities. With a full bladder there is a relative predominance of parasympathetic nerve activity, whereas sympathetic activity is essential at the end of bladder filling to control the sphincter and suppress bladder contraction. There are different kinds of parameters for HRV and RMSSD (square root of the mean of the sum of the squares of differences between adjacent RR interval) is used herein. A RR interval is the interval between successive R's, where R is a point corresponding to the peak of the QRS complex of the ECG wave. It can measure short-term variation in the RR interval because it is entirely based on comparisons between successive beats.

As used herein, a "wireless transmission" is the transmission of information between two points not connected by an electrical connector. Examples of wireless transmission include, but not limited to, wi-fi transmission, BLUETOOTH transmission, radio frequency (RF) transmission, infrared (IR) transmission and $3^{rd}$ generation (3G) or $4^{th}$ generation (4G) of mobile telecommunications technology.

What is claimed is:

1. A device for detecting fullness of a bladder of a subject, comprising:
   a distension sensor that is located on a waistband of a pant and that detects changes to a curvature of skin adjacent the bladder of the subject;
   an electromyography (EMG) sensor that is located in the pant and that includes two EMG electrodes that detect potential difference caused by contractions of the bladder of the subject;
   a heart sensor that is located in the pant and that detects a heart rate variability (HRV) of a heart of the subject; and
   a microcontroller that processes signals received from the distension sensor, the EMG sensor and the heart sensor, and generates, based on the signals, an output value that indicates the fullness of the bladder, wherein the output value is generated based on the Equation Output value=−22+31*Distension+1.77*Heart Rate Variability−3.07*Amplitude of EMG.

2. The device of claim 1, wherein the microcontroller generates the output value based on static parameters of the subject that include age and weight and based on data from the distention sensor and the EMG sensor.

3. The device of claim 1 further comprising:
an alert module that communicates with the microcontroller and generates an audio or visual alert when the fullness of the bladder reaches a predetermined threshold value.

4. The device of claim 1, wherein the EMG sensor is located on a crotch of the pant.

5. The device of claim 1, wherein the output value indicates a percentage of the fullness of the bladder.

6. The device of claim 1 further comprising:
a transmitter that communicates with the microcontroller and that wirelessly transmits the output value to an electronic device that is remote from the pant, wherein the electronic device indicates the fullness of the bladder.

7. A method of measuring a fullness of a bladder of a person wearing an undergarment, the method comprising:
sensing, with an electromyography (EMG) sensor provided in the undergarment worn by the person, changes in electric potential of the bladder of the person;
sensing, with a distension sensor provided in the undergarment worn by the person, changes in curvature of the bladder of the person;
sensing, with an infrared sensor provided in the undergarment worn by the person, heart rate variability (HRV) of the person; and
analyzing, with a microcontroller provided in the undergarment worn by the person, data from the EMG sensor, data from the distension sensor and data from the infrared sensor, to generate an output value that indicates the fullness of the bladder of the person,
wherein the output value is generated based on the Equation Output value=−22+31*Distension+1.77*Heart Rate Variability−3.07*Amplitude of EMG.

8. The method of claim 7, further comprising:
estimating, with the microcontroller, a percentage of the fullness of the bladder of the person based on dynamic parameters that include the data from the EMG sensor and the data from the distention sensor and based on static parameters that include data of an age of the person, a gender of the person, and a weight of the person.

9. The method of claim 7, further comprising:
alerting, with an alert module provided in the undergarment worn by the person, the person with an alert when the fullness of the bladder of the person reaches a threshold value.

10. The method of claim 7 further comprising:
calculating, by the microcontroller, an output value based on the data from the EMG sensor and the data from the distention sensor; and
wirelessly transmitting, from a transmitter provided in the undergarment worn by the person, the output value to an electronic device that is external from the undergarment, wherein the output value provides an indication of the fullness of the bladder of the person.

11. The method of claim 7 further comprising:
positioning the EMG sensor in the undergarment such that the EMG sensor is located adjacent an anus of the person when the undergarment is worn by the person.

12. The method of claim 7 further comprising:
vibrating, with a vibration sensor provided in the undergarment worn by the person, to provide the person with a vibrational alert when the fullness of the bladder of the person reaches a threshold value.

13. An undergarment that determines fullness of a bladder of a person, the undergarment comprising:
an electromyography (EMG) sensor, provided in the undergarment worn by the person, that senses changes in electric potential of the bladder of the person;
a distention sensor, provided in the undergarment worn by the person, that senses a curvature of the bladder of the person;
an infrared sensor, provided in the undergarment worn by the person, that measures a heart rate variability (HRV) of the person; and
a microcontroller, provided in the undergarment worn by the person, that analyzes data received from the EMG sensor, from the distention sensor and from the infrared sensor to generate an output that indicates the fullness of the bladder of the person,
wherein the output value is generated based on the Equation Output value=−22+31*Distension+1.77*Heart Rate Variability−3.07*Amplitude of EMG.

14. The undergarment of claim 13, further comprising:
an alert module, provided in the undergarment worn by the person, that vibrates when the microcontroller determines that the fullness of the bladder of the person reaches a threshold value.

15. The undergarment of claim 13, further comprising:
a wireless transmitter, provided in the undergarment worn by the person, that transmits an alert signal to an electronic device in wireless communication with the wireless transmitter when the microcontroller determines that the fullness of the bladder of the person reaches a threshold value.

16. The undergarment of claim 13, wherein the microcontroller generates an output value that indicates the fullness of the bladder of the person based on static parameters of the person that include age and weight and based on data from the distention sensor and the EMG sensor.

17. The undergarment of claim 13, wherein the EMG sensor is located on a crotch of the undergarment.

* * * * *